United States Patent [19]
Schnorrenberg et al.

[11] Patent Number: 4,555,511
[45] Date of Patent: Nov. 26, 1985

[54] THIENO [3,2,C]PYRIDINES USEFUL AS ANTIHYPERTENSIVES

[75] Inventors: Gerd Schnorrenberg, Ingelheim am Rhein; Otto Roos, Schwabenheim; Walter Lösel; Ingrid Wiedemann, both of Gau-Algesheim; Wolfram Gaida, Ingelheim am Rhein; Wolfgang Hoefke, Wiesbaden, all of Fed. Rep. of Germany

[73] Assignee: Boehringer Ingelheim KG, Ingelheim am Rhein, Fed. Rep. of Germany

[21] Appl. No.: 572,179

[22] Filed: Jan. 19, 1984

[30] Foreign Application Priority Data

Jan. 22, 1983 [DE]  Fed. Rep. of Germany ....... 3302125

[51] Int. Cl.$^4$ ........................................... C07D 513/02
[52] U.S. Cl. .................................... 514/301; 546/114
[58] Field of Search ......................... 546/114; 424/256

[56] References Cited
FOREIGN PATENT DOCUMENTS 0099802  2/1984  France ................................ 424/256

Primary Examiner—Henry R. Jiles
Assistant Examiner—P. Ann Bucci
Attorney, Agent, or Firm—Hammond & Littell, Weissenberger & Dippert

[57] ABSTRACT

Compounds of the formula

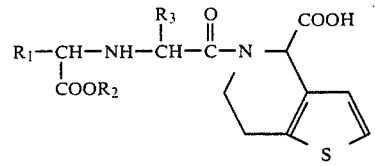

wherein
$R_1$ is hydrogen, alkyl of 1 to 6 carbon atoms or phenyl (alkyl of 1 to 6 carbon atoms);
$R_2$ is hydrogen, alkyl of 1 to 4 carbon atoms or phenyl (alkyl of 1 to 6 carbon atoms);
$R_3$ is hydrogen or alkyl of 1 to 6 carbon atoms; and their use as antihypertensives.

7 Claims, No Drawings

THIENO [3,2,C]PYRIDINES USEFUL AS ANTIHYPERTENSIVES

This invention relates to novel amino acid derivatives and non-toxic salts thereof, to methods of preparing these compounds, to pharmaceutical compositions containing them as active ingredients, and to a method of using them as antihypertensives.

More particularly, the present invention relates to a novel class of compounds represented by the formula

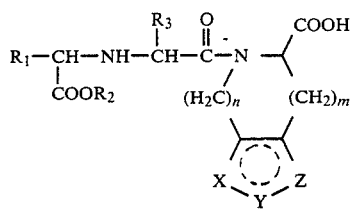

wherein
$R_1$ represents hydrogen, alkyl of 1 to 6 carbon atoms or phenylalkyl of 7 to 12 carbon atoms;
$R_2$ represents hydrogen, alkyl of 1 to 4 carbon atoms or phenylalkyl of 7 to 12 carbon atoms;
$R_3$ represents hydrogen or alkyl of 1 to 6 carbon atoms;
n and m each represent 0, 1 or 2, the sum of n and m being 1 or 2;
X, Y and Z each represent oxygen, sulfur, $-NR_4-$, $=CR_5-$, $-CHR_5-$,

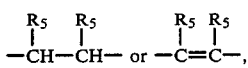

provided that only one of the radicals X, Y and Z can represent O, S,

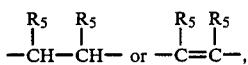

and one or two of the radicals X, Y and Z can represent $-NR_4-$;
$R_4$ represents hydrogen or alkyl of 1 to 4 carbon atoms; and
$R_5$ represents hydrogen or, together with a vicinal radical $R_5$, a phenyl ring, or in case m and n = 1, the dihydro form with its double bond in conjugation to the C-terminal carboxylic group.

The five- or six-membered heterocycles condensed on the pyrrolidino- or piperidino-carboxylic acid can be saturated or unsaturated. Preferred heterocycles are: furan, pyrrole, thiophene, benzofuran, indole, benzothiophene, oxazole, imidazole, thiazole, isoxazole, pyrazole, pyrrolidine, tetrahydrofuran, tetrahydrothiophene, pyridine, pyridazine, quinoline, isoquinoline or piperidine.

The new compounds generally have several asymmetric centers and may therefore be present as diastereoisomers or in the form of racemates or racemic mixtures. The invention embraces both the racemic mixtures and the individual diastereoisomers. Those enantiomers in which the symmetric carbon atoms are present in the L-configuration are preferred.

The compounds of formula I can be present as internal salts or, if there are free carboxyl groups, as alkali metal or alkaline earth metal salts, for example as sodium, potassium, magnesium or calcium salts, or as non-toxic salts with amines such as trimethylamine or dicyclohexylamine. Furthermore, a free amino group present can be reacted with a mineral acid, such as hydrochloric acid or hydrobromic acid, or an organic acid, for example acetic acid, to form a non-toxic acid addition salt.

The compounds of the formula I can be prepared by the following methods:

Method A

By reacting a compound of the formula

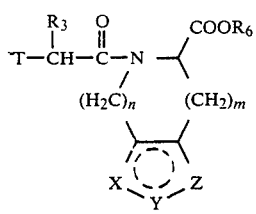

with a compound of the formula

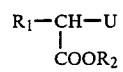

where
T represents a nucleofuge group, and
U represents an amino group or, conversely, T represents an amino group and U a nucleofuge group,
$R_6$ represents hydrogen, alkyl of 1 to 4 carbon atoms, a benzyl group or a trimethylsilyl group, and
$R_1$, $R_2$, $R_3$, n, m, X, Y and Z have the meanings given above.

Halides can serve as nucleofuges, so that, for example, the process can start from 2-halo-carboxylic acid derivatives and 2-amino acid derivatives. The reaction is preferably carried out in polar solvents such as water, alcohols, dimethylformamide, acetonitrile, dimethylsulfoxide or mixtures thereof, optionally in the presence of an alkali metal or alkaline earth metal carbonate, tertiary amines, quaternary ammonium hydroxides or tetraalkylguanidines. After $R_6$ has been splitt off according to conventional methods, for example by acid or alkaline hydrolysis of the ester or catalytic hydrogenation, the end products of the formula I are obtained.

Method B

By reacting an α-oxocarboxylic acid derivative of the formula

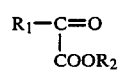

in which $R_1$ and $R_2$ have the meanings mentioned above, with an amino acid amide of the formula II ($T=NH_2$), described in method A to form the corresponding imine which is reduced. Suitable solvents for this reaction are water or alcohols, but also non-polar solvents such as benzene or toluene. When anhydrous solvents are used, the reaction water can be bound by addition of a molecular sieve. The reduction can be carried out by means of sodium borohydride, sodium cyanoborohydride or catalytic hydrogenation with palladium-on-charcoal or Raney nickel as catalysts.

By splitting off $R_6$ according to conventional methods, such as described by way of the examples below, the end products of the formula I are obtained.

Method C

Starting from a compound of the formula

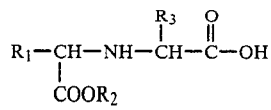

in which $R_1$, $R_2$ and $R_3$ have the meanings given above, by reaction with an amino acid of the formula

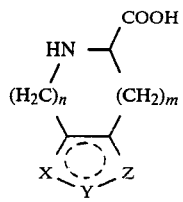

in which X, Y and Z and n and m have the meanings given above, or by reaction with an ester of a compound of the formula VI ($R_6$ instead of hydrogen).

Condensation can be carried out according to methods described in Houben-Weyl, Methods of Organic Chemistry, Volume 15. A preferred condensation agent for the reaction is N,N'-dicyclohexyl-carbodiimide, and a preferred carboxyl protective group for the amino acid VI is the tert.butyl-, benzyl- or trimethylsilyl group. After condensation has been carried out, this can be split off according to the conventional methods such as those described in the examples below.

The starting compounds II (T=halogen) are obtainable by condensation of esters of amino acids of the formula VI with 2-halocarboxylic acids via their corresponding acid chlorides, mixed anhydrides, active esters or by other methods described in Houben-Weyl, Methods of Organic Chemistry, Volume 15.

The compounds II (T=NH$_2$) are obtained by reacting esters of amino acids with N-protected amino-carboxylic acids. Those amino protection groups and condensation agents described in Houben-Weyl, Methods of Organic Chemistry, Volume 15, are used. The benzyloxycarbonyl or the fluorenylmethoxycarbonyl group are preferably used as amino protective groups, and N,N'-dicyclohexylcarbodiimide is preferably used as the condensation agent.

The starting compounds of the formula VI can be obtained, depending on the meaning of the radicals X, Y and Z, for example by reacting
(a) tryptamine and glyoxylic acid [B. T. Ho et al., J. Pharm. Sci. 57, 269–275 (1968)],
(b) thiophene-2-ethylamine and glyoxylic acid [J. P. Moffrand, Heterocycles 16, 35–37 (1981)],
(c) tryptophan and formaldehyde [D. G. Harvey et al., J. Chem. Soc. 1941, 153–159],
(d) Histidine and formaldehyde [M. Cain et al., Heterocycles 19, 1003–1007 (1982)].

In the methods described above, the starting compounds can be present in the form of racemic mixtures, diastereoisomers or enantiomers. If there are racemic mixtures, the sterically unitary forms can be enriched or obtained pure from the reaction products according to conventional methods such as fractional crystallization or chromatographic processes.

The following can be obtained, for example, according to the methods described above:
N-[N-(1-methoxycarbonyl-3-phenylpropyl)-L-alanyl]-4,5,6,7-tetrahydro-thieno[3,2-c]pyridine-4-carboxylic acid,
N-[N-(1-carboxy-2-phenylethyl)-alanyl]-4,5,6,7-tetrahydro-thieno[3,2-c]pyridine-4-carboxylic acid,
N-[N-(1-methoxycarbonyl-3-phenylpropyl)-alanyl]-4,5,6,7-tetrahydro-thieno[2,3-c]pyridine-7-carboxylic acid,
N-[N-(1-ethoxycarbonyl-3-phenylpropyl)-L-alanyl]-L-2,3,4,9-tetrahydro-1H-pyrido[3,4-b]indole-3-carboxylic acid,
N-[N-(1-methoxycarbonyl-3-phenylpropyl)-alanyl]-L-2,3,4,9-tetrahydro-1H-pyrido[3,4-b]indole-3-carboxylic acid,
N-[N-(L-1-ethoxycarbonyl-3-phenylpropyl)-L-alanyl]-L-2,3,4,9-tetrahydro-1H-pyrido[3,4-b]indole-1-carboxylic acid,
N-[N-(L-1-carboxy-2-methylpropyl)-alanyl]-L-2,3,4,9-tetrahydro]-1H-pyrido[3,4-b]indole-3-carboxylic acid,
N-[N-(1-ethoxycarbonylmethyl)-L-alanyl]-2,3,4,9-tetrahydro-1H-pyrido[3,4-b]indole-1-carboxylic acid,
N-[N-(L-1-ethoxycarbonyl-3-phenylpropyl)-L-alanyl]-L-4,5,6,7-tetrahydro-thieno[2,3-c]pyridine-7-carboxylic acid,
N-[N-(1-carboxy-3-phenylpropyl)-L-alanyl]-4,5,6,7-tetrahydro-pyrrolo[2,3-c]pyridine-7-carboxylic acid,
N-[N-(1-ethoxycarbonyl-3-phenylpropyl)-L-alanyl]-5,6,7,8-tetrahydro-pyrido[4,3-b]pyridine-5-carboxylic acid,
N-[N-(1-carboxy-3-phenylpropyl)-L-alanyl]-L-4,5,6,7-tetrahydro-1H-imidazo[4,5-c]pyridine-6-carboxylic acid,
N-[N-(L-1-ethoxycarbonyl-3-phenylpropyl)-L-alanyl]-4,5,6,7-tetrahydro-thieno[3,2-c]pyridine-L-4-carboxylic acid,
N-[N-(L-1-carboxy-3-phenylpropyl)-L-alanyl-4,5,6,7-tetrahydro-thieno[3,2-c]pyridine-L-4-carboxylic acid,
N-[N-(L-1-ethoxycarbonyl-3-phenylpropyl)-L-alanyl]-4,5-dihydro-thieno[3,2-c]pyridine-6-carboxylic acid,
N-[N-(L-1-carboxy-3-phenylpropyl)-L-alanyl]-6,7-dihydro-thieno[2,3-c]pyridine-5-carboxylic acid,
N-[N-(L-1carboxy-3-phenylpropyl)-L-alanyl]-4,5-dihydro-thieno[3,2-c]pyridine-6-carboxylic acid.

The following examples illustrate the present invention and will enable others skilled in the art to understand it more completely. It should be understood, however, that the invention is not limited solely to the particular examples given below.

EXAMPLE 1

N-[N-(1-Methoxycarbonyl-3-phenylpropyl)-alanyl]-L-2,3,4,9-tetrahydro-1H-pyrido[3,4-b]indole-3-carboxylic acid 15 g of L-2,3,4,9-tetrahydro-1H-pyrido[3,4-b]indole-3-carboxylic acid were refluxed for 2 hours with 7.5 g of chlorotrimethylsilane in 200 ml of anhydrous tetrahydrofuran. The mixture was cooled to 0° C., 15 g of triethylamine were added and mixed dropwise at 0° C. with a solution of 17 g of 2-bromopropionic acid chloride in 50 ml of anhydrous tetrahydrofuran, and stirred for one hour at 0° C. and overnight at room temperature. The precipitate was filtered off, the filtrate was evaporated in vacuo, the residue was dissolved in ethyl acetate and extracted with KHSO₄ and NaHCO₃ solution. The combined NaHCO₃ phases were acidified with 2N HCl and extracted with dichloromethane. The combined dichloromethane phases were washed with a saturated NaCl solution, dried over MgSO₄ and evaporated in vacuo. The residual colorless oil (18 g) was stirred for 24 hours at room temperature in 100 ml of anhydrous dimethylformamide with 11.5 g of methyl 2-amino-4-phenylbutyrate hydrochloride, 1 g of potassium iodide and 10 g of triethylamine. The dimethylformamide was distilled off in vacuo, the residue was dissolved in ethyl acetate, washed with water, KHSO₄ solution and water, dried over MgSO₄ and evaporated. The residue was chromatographed on silica gel [eluant: dichloromethane, methanol, ethyl acetate (20:1:2)]. 13.9 g (60% of theory) of the title compound were isolated as a colorless oil.

¹H-NMR [CD₃OD]: δ=1.67 ppm, dd [3H], J=7 Hz; 2.0 m [2H]; 2.7 t [2H], J=7 Hz; 3.2–3.8 m [4H]; 3.7 s [3H]; 4.5–5.5 m [3H]; 6.6–7.6 m [9H].

EXAMPLE 2

N-[N-(1-Methoxycarbonyl-3-phenylpropyl)-alanyl]-4,5,6,7-tetrahydro-thieno[2,3-c]pyridine-7-carboxylic acid 10.4 g of 2-bromopropionyl chloride and 30 ml of 2N caustic soda were added dropwise at the same time to a solution, cooled to 0° C., of 10.8 g of 4,5,6,7-tetrahydro-thieno[2,3-c]pyridine-7-carboxylic acid in 60 ml of 1N caustic soda, and the mixture was subsequently stirred for 2 hours at room temperature. The solution was extracted with ethyl acetate, and the aqueous phase was acidified with 2N HCl and extracted with dichloromethane. The combined organic phases were washed with saturated NaCl solution, dried over MgSO₄ and evaporated. The residue was triturated in a little ethyl acetate and suction-filtered off. The colorless crystals (13.3 g) were stirred for 24 hours at room temperature in 80 ml of anhydrous dimethylformamide with 9.6 g of methyl 2-amino-4-phenylbutyrate hydrochloride, 0.8 g of potassium iodide and 8.4 g of triethylamine. The dimethylformamide was distilled off in vacuo, the residue was dissolved in ethyl acetate, washed with water, KHSO₄ solution and water, dried over MgSO₄ and evaporated. The residue was chromatographed on silica gel [eluant: dichloromethane, methanol, ethylacetate (100:1:10)]. 11.3 g (=63% of theory) of the title compound were obtained as a colorless oil.

MS: m/e=430 (M+), 412, 327.

EXAMPLE 3

N-[N-(L-1-Ethoxycarbonyl-3-phenylpropyl)-L-alanyl]-L-4,5,6,7-tetrahydro-thieno[2,3-c]-pyridin-7-carboxylic acid 6.2 g of N-fluorenylmethoxycarbonyl-L-alanine were mixed in 50 ml of anhydrous dichloromethane at 0° C. with 4.5 g of dicyclohexylcarbodiimide, and after 15 minutes 4.6 g of tert. butyl 4,5,6,7-tetrahydro-thieno[2,3-c]pyridine-7-carboxylate were added and stirred for a further 30 minutes at 0° C. and 6 hours at room temperature. The mixture was filtered off, and the filtrate was washed with a saturated KHSO₄ solution, NaHCO₃ solution and water, dried over MgSO₄ and evaporated in vacuo. The oily residue was chromatographed by means of a medium-pressure chromatography on Merck LiChroprep/Si 60 [eluant: cyclohexane/ethyl acetate (3:1)], whereby separation into the diastereoisomers occurred. The fourth fraction (4.2 g =42% of theory) was allowed to stand for 2 hours at room temperature in 40 ml of dimethylformamide/piperidine (4:1). The dimethylformamide and piperidine wwere distilled off, and the residue was chromatographed on silica gel [eluant: toluene, ethyl acetate, formic acid (9:5:1)]. 2.3 g of the product were stirred at room temperature for 24 hours in 20 ml of anhydrous dimethylformamide with 2 g of ethyl 2-bromo-4-phenylbutyrate, 0.2 g of potassium iodide and 0.75 g of triethylamine. The dimethylformamide was distilled off in vacuo, the residue was dissolved in ethyl acetate, washed with water, KHSO₄ solution and water, dried over MgSO₄ and evaporated. The residue was chromatographed by means of medium-pressure chromatography on Merck LiChroprep/Si 60 [eluant: dichloromethane, methanol, ethylacetate (100:1:1)]. Separation of the diastereoisomers occurred. The corresponding fraction was stirred for 30 minutes at room temperature in 20 ml of 1N HCl in glacial acetic acid. The glacial acetic acid was distilled off in vacuo, and the residue was re-evaporated several times with toluene. 1.6 g (49% of theory) of the hydrochloride of the title compound were obtained. MS: m/e=426 (M+), 412, 327.

EXAMPLE 4

N-[N-(L-1-Ethoxycarbonyl-3-phenylpropyl)-L-alanyl]-L-2,3,4,9-tetrahydro-1H-pyrido[3,4-b]indole-1-carboxylic acid 40.6 g of ethyl 2-bromo-4-phenyl-butyrate were stirred at room temperature with 40.6 g of L-alanine-tert. butylester and 20 g of triethylamine in 200 ml of anhydrous dimethylformamide. The mixture was evaporated in vacuo, the residue was dissolved in ethyl acetate, washed with water, dried over MgSO₄ and evaporated in vacuo. The residue was chromatographed on silica gel [eluant: toluene, ethyl acetate, formic acid (9:5:1)], whereby separation of the diastereoisomers occurred. After the solvent had been evaporated, the corresponding fraction was stirred for 30 minutes at room temperature with 50 ml of 1N HCl in glacial acetic acid. The mixture was evaporated in vacuo and triturated with ether, 12.5 g (45% of theory) of colorless crystals being obtained. These were stirred with 12.2 g of tert.butyl 2,3,4,9-tetrahydro-1H-pyrido[3,4-b]indole-1-carboxylate, 6 g of 1-hydroxybenzotriazole and 9.3 g of dicyclohexylcarbodiimide in 100 ml of dimethylformamide for 30 minutes at 0° C. and for 2 hours at room temperature. The urea was filtered off, the dimethylformamide was distilled off in vacuo, the residue was taken up in ethyl acetate, washed with water, dried over MgSO₄ and evaporated in vacuo. The residue was chromatographed on silica gel [eluant: cyclohexane, ethyl acetate (3:1)]. Separation of the diastereoisomers occurred. The corresponding fraction was stirred for 30 minutes at room temperature with 50 ml of 1N HCl in glacial acetic acid. The glacial acetic acid was evaporated, and the residue was re-evaporated with toluene. 7 g (30% of theory) of the hydrochloride of the title compound were obtained in this way.

EXAMPLE 5

N-[N-(1-Carboxy-3-phenylpropyl)-L-alanyl]-L-4,5,6,7-tetrahydro-1H-imidazo[4,5-c]pyridine-6-carboxylic acid 11.2 g of N-benzyloxycarbonyl-L-alanine, 11.1 g of tert.butyl L-4,5,6,7-tetrahydro-1H-imidazo[4,5-c]pyridine-1-carboxylate and 11.3 g of dicyclohexylcarbodiimide were stirred in 100 ml of anhydrous dichloromethane for 30 minutes at 0° C. and for 6 hours at room temperature. The urea was filtered off, and the filtrate was washed with KHSO$_4$, NaHCO$_3$ solution and water, dried over MgSO$_4$ and evaporated. The residue was dissolved in glacial acetic acid and hydrogenated with 1 g of palladium-on-charcoal and hydrogen. The glacial acetic acid was distilled off, the residue was triturated with diethyl ether and suction-filtered off. 11.7 g (80% of theory) of the resulting colorless crystals were dissolved with 28.4 g of 2-oxo-4-phenylbutyric acid in 50 ml of ethanol/water (1:1) and mixed at room temperature dropwise with a solution of 8 g of sodium cyanoborohydride in 20 ml of ethanol/water (1:1). The mixture was stirred overnight and poured over a Dowex 50 W×4 (50–100 mesh) ion exchanger. It was washed with ethanol/water (1:1) and eluted with ethanol/water (1:1) with 2% pyridine. 13.3 g (73% of theory) of the tert. butylate were stirred for 30 minutes at room temperature with 50 ml of 1N HCl in glacial acetic acid, the glacial acetic acid was distilled off and re-evaporation was carried out with toluene. 10 g (58% of theory) of the hydrochloride of the title compound, m.p. 163°–170° C., were obtained.

EXAMPLE 6

N-[N-(L-1-Carboxy-3-phenylpropyl)-L-alanyl]-6,7-dihydro-thieno[2,3-c]pyridine-5-carboxylic acid 650 mg of dicyclohexylcarbodiimide were added to a solution of 716 mg of methyl 6,7-dihydro-thieno[2,3-c]-pyridine-5-carboxylate hydrochloride, 1 g of N-(L-ethoxycarbonyl-3-phenylpropyl)-L-alanine, 0.5 g of 1-hydroxybenzotriazole and 620 mg of triethylamine in 50 ml tetrahydrofuran/dimethylformamide (1:1), cooled to 0° C. The mixture was stirred for one hour at 0° C. and for 24 hours at room temperature, then the solvent evaporated in vacuo, and the residue was dissolved in ethyl acetate. The solution was washed with saturated NaHCO$_3$ solution and 0.001 N HCl, dried over MgSO$_4$ and evaporated. The residue was allowed to stand in acetonitrile for 24 hours at 0° C., then the precipitated dicyclohexylurea was filtered off, the solvent was evaporated, and the residue was chromatographed on silica gel (eluant: ethylacetate/n-hexane 1:1). The methyl N-[N-(L-1-ethoxycarbonyl-3-phenylpropyl)-L-alanyl]-6,7-dihydro-thieno[2,3-c]pyridine-5-carboxylate thus obtained was stirred overnight with 1N NaOH/acetonitrile. The acetonitrile was distilled off, the aqueous solution was extracted with ethyl acetate, acidified to pH 3 with 1N HCl and filtered.

620 mg (53% of theory) of the title compound were obtained as colorless crystals, m.p. 154° C.

EXAMPLE 7

N-[N-(L-1-Carboxy-3-phenylpropyl)-L-alanyl]-4,5-dihydro-thieno[3,2-c]pyridine-6-carboxylic acid Using the method described in Example 6, 1 g (60% of theory) of the title compound, m.p. 161° C., were obtained as colorless crystals, starting from 924 mg of methyl 4,5-dihydro-thieno[3,2-c]pyridine-6-carboxylate hydrochloride, 1.3 g of N-(L-1-ethoxycarbonyl-3-phenylpropyl)-L-alanine, 645 mg of 1-hydroxybenzotriazole and 840 mg of dicyclohexylcarbodiimide.

EXAMPLE 8

N-[N-(L-1-Ethoxycarbonyl-3-phenylpropyl)-L-alanyl]-4,5-dihydro-thieno[3,2-c]pyridine-6-carboxylic acid 456 mg of methyl N-[N-(L-1-ethoxycarbonyl-3-phenylpropyl)-L-alanyl]-4,5-dihydro-thieno[3,2-c]pyridine-6-carboxylate (see Example 7) were stirred at room temperature with 1 ml of 1N NaOH in acetonitrile/water for 48 hours at room temperature. Then the solvent was evaporated, the aqueous residue was acidified with 1N HCl and extracted with ethyl acetate. The ethyl acetate phase was dried, and the solvent was evaporated. 243 mg (55% of theory) of the title compound are obtained as a colorless oil.

EXAMPLE 9

N-[N-(L-1-Carboxy-3-phenylpropyl)-L-alanyl]-4,5,6,7-tetrahydro-thieno[3,2-c]pyridine-L-4-carboxylic acid 18.5 g of dicyclohexyl urea were added at 0° C. to 17.3 g of methyl DL-4,5,6,7-tetrahydro-thieno[3,2-c]pyridine- 4-carboxylate hydrochloride, 23.7 g of N-(L-1-ethoxycarbonyl-3-phenylpropyl)-L-alanine, 11.3 g of hydroxybenzotriazole and 15 g of triethylamine in 300 ml dimethylformamide/tetrahydrofuran (1:2). The mixture was stirred for one hour at 0° C. and for 24 hours at room temperature, filtered and evaporated in vacuo. The residue was dissolved in ethyl acetate, washed with a saturated solution of NaHCO$_3$ and then with 0.001 N HCl, dried and evaporated. The residue was allowed to stand for 24 hours at 0° C. in acetonitrile, the precipitated dicyclohexyl urea was filtered off, the solution was evaporated, and the residue was chromatographed on silica gel (eluant: ethyl acetate/n-hexane 1:1), whereby separation into the diastereoisomers occurred. The fraction containing methyl N-[N-(L-1-ethoxycarbonyl-3-phenylpropyl)-L-alanyl]-4,5,6,7-tetrahydro-thieno[3,2-c]pyridine-L-4-carboxylate was stirred at room temperature in acetonitrile with 1N NaOH for 24 hours, extracted with ethyl acetate, acidified with 1N HCl to pH 3 and filtered. 13.4 g of the title compound were obtained as a colorless powder, m.p. 166°–167° C.

Using the procedure of Example 9, the following end products of the formula I were also obtained:

N-[N-(L-1-carboxy-3-phenylpropyl)-L-alanyl]-4,5,6,7-tetrahydro-thieno[2,3-c]pyridine-L-7-carboxylic acid, m.p. 169° C.;

N-[N-(L-1-carboxy-3-phenylpropyl)-L-alanyl]-4,5,6,7-tetrahydro-1H-imidazo[4,5-c]pyridine-L-6-carboxylic acid, m.p. 180° C. (dec.)—MS: m/e=382 (M$^+$-H$_2$O);

N-[N-(L-1-carboxy-3-phenylpropyl)-L-alanyl]-2,3,4,9-tetrahydro-1H-pyrido[3,4-b]indole-L-1-carboxylic acid, m.p. 175°–176° C.;

N-[N-(L-1-carboxy-3-phenylpropyl)-L-alanyl]-2,3,4,9-tetrahydro-1H-pyrido[3,4-b]indole-L-3-carboxylic acid, m.p. 190° C.;

N-[N-(L-1-carboxy-3-phenylpropyl)-L-alanyl]-4,5,6,7-tetrahydro-thieno[3,2-c]pyridine-L-6-carboxylic acid, m.p. 157° C.;

N-[N-(L-1-carboxy-3-phenylpropyl)-L-alanyl]-4,5,6,7-tetrahydro-thieno[2,3-c]pyridine-L-5-carboxylic acid, m.p. 155°–157° C.

EXAMPLE 10

N-[N-(L-1-Ethoxycarbonyl-3-phenylpropyl)-L-alanyl]-4,5,6,7-tetrahydro-thieno[3,2-c]pyridine-L-4-carboxylic acid Using the procedure of Example 8, 3.1 g of the title compound (70% of theory) were obtained from 4.6 g of methyl N-[N-(L-1-ethoxycarbonyl-3-phenylpropyl)-L-alanyl]-4,5,6,7-tetrahydro-thieno[3,2-c]pyridine-L-4-carboxylate (described as intermediate in Example 9) and 10 ml of 1N NaOH as a colorless powder, m.p. 133°–135° C.

EXAMPLE 11

N-[N-(L-1-Ethoxycarbonyl-3-phenylpropyl)-L-alanyl]-4,5,6,7-tetrahydro-thieno[2,3-c]pyridine-L-7-carboxylic acid Using the procedure of Example 8, 2.4 g of the title compound (55% of theory) were obtained from 4.6 g of methyl N-[N-(L-1-ethoxycarbonyl-3-phenylpropyl)-L-alanyl]-4,5,6,7-tetrahydro-thieno[2,3-c]pyridine-L-7-carboxylate and 10 ml of 1N NaOH as a colorless powder, m.p. 75° C. (dec.).

The new end products of the formula I exhibit strong, long-lasting hypotensive activity. This is based on an inhibition of the angiotensin I-converting enzyme and consequent blocking of the formation of the vasoconstrictor angiotensin II from angiotensin I. Furthermore, the new compounds have an inhibiting effect on the enzyme kininase II which is responsible for bradykinin decomposition and which is considered identical to the converting enzyme mentioned above. Since bradykinin has a vasodilatory effect, the hypotensive effect is reinforced by this additional effect. The lowering of blood pressure in normal rats, which is produced by means of bradykinin, is reinforced by the new compounds.

Administration can be intravenous, subcutaneous or oral. The dosage in oral administration is around 20–200 mg per individual dose. For intravenous administration, or in simultaneous administration with diuretics, it is appropriate to reduce the dose.

For use in therapy, the new compounds are mixed with conventional pharmaceutical fillers or carriers, extenders, disintegrating agents, binders, entrainers, thickeners or diluents.

The pharmaceutical preparation forms to be considered are, for example, tablets, capsules, suppositories, solutions, juices, emulsions or dispersable powders, and if desired further known active substances, for example, saluretics, diuretics and/or anti-hypotonics, can be added.

Appropriate tablets can be obtained, for example, by mixing the active substance or substances with known excipients, for example inert diluents, such as calcium carbonate, calcium phosphate or lactose, disintegrating agents, such as corn starch or algenic acid, binders such as starch or gelatin, lubricants such as magnesium stearate or talc, and/or agents for achieving a sustained-release effect, such as carboxypolymethylene, carboxymethylcellulose, cellulose acetate phthalate or polyvinyl acetate. The tablets can also consist of several layers.

Correspondingly, coated tablets can be prepared by covering cores produced analogous to the tablets with agents used conventionally in coated tablet coverings, for example polyvinylpyrrolidone or shellac, gum arabic, talc, titanium dioxide or sugar. To achieve a sustained-release effect or to prevent incompatibilities, the core can also consist of several layers. Likewise, the coated tablet envelope can consist of several layers to achieve a sustained-release effect, and the excipients mentioned above as regards the tablets can be used.

Juices of the active substances or active substance combinations according to the invention can additionally also contain a sweetener, such as saccharin, cyclamate, glycerol or sugar, and a flavor improving agent, for example, aromatics such as vanillin or orange extract. They can also contain suspension excipients or thickeners, such as sodium carboxymethyl cellulose, wetting agents, for example condensation products of fatty alcohols with ethylene oxide, or protective substances, such as p-hydroxybenzoates.

Injection solutions are prepared in a conventional way, for example by adding preserving agents, such as p-hydroxybenzoates, or stabilizers, such as alkali metal salts of ethylenediamine tetraacetic acid, and by adding suitable solubilizers, and can be filled into injection bottles or ampules.

Capsules containing one or more active substances or active-substance combinations can be prepared, for example, by mixing the active substances with inert carriers, such as lactose or sorbitol, and encapsulating them in gelatin capsules.

The following examples illustrate a few pharmaceutical compositions comprising a compound of the present invention as an active ingredient and represent the best modes contemplated of using the invention. The parts are parts by weight unless otherwise specified.

EXAMPLE 12

Coated tablets

The tablet core composition is compounded from the following ingredients:

| | |
|---|---|
| N—[N—(L-1-ethoxycarbonyl-3-phenyl-propyl)-L-alanyl]-4,5,6,7-tetra-hydro-thieno[3,2-c]pyridine-L-4-carboxylic acid | 100.0 parts |
| Lactose | 60.0 parts |
| Corn starch | 35.0 parts |
| Gelatin | 3.0 parts |
| Magnesium stearate | 2.0 parts |
| Total | 200.0 parts |

Preparation:

The mixture of the active ingredient with lactose and corn starch is granulated with an aqueous 10% gelatin solution through a screen with a mesh width of 1 mm, dried at 40° C. and again passed through the screen. The granulate obtained in this way is mixed with magnesium stearate, and the mixture is processed into 200 mg-tablet cores. The cores obtained in this way are covered in conventional manner with a thin shell consisting of a mixture of sugar, titanium dioxide, talc and gum arabic. The finished coated tablets are polished with beeswax.

EXAMPLE 13

Tablets

The tablet composition is compounded from the following ingredients:

| | |
|---|---|
| N—[N—(L-1-carboxy-3-phenylpropyl)-L-alanyl]-4,5,6,7-tetrahydro-thieno-[3,2-c]pyridine-L-4-carboxylic acid | 100.0 parts |

-continued

| | |
|---|---|
| Lactose | 70.0 parts |
| Corn starch | 50.0 parts |
| Soluble starch | 7.0 parts |
| Magnesium stearate | 3.0 parts |
| Total | 230.0 parts |

Preparation:

The active ingredient and magnesium stearate are granulated with an aqueous solution of the soluble starch, the granulate is dried and mixed intimately with lactose and corn starch. The mixture is then compressed into tablets weighing 230 mg, each of which contains 100 mg of active ingredient.

EXAMPLE 14

Hypodermic solution

The solution is compounded from the following ingredients:

| | |
|---|---|
| N—[N—(L-1-ethoxycarbonyl-3-phenyl-propyl)-L-alanyl]-4,5-dihydro-thieno[3,2-c]pyridine-6-carboxylic acid | 50.0 parts |
| Ethanolamine | 60.0 parts |
| Sodium chloride | 20.0 parts |
| Distilled water q.s. ad | 2000.0 parts by vol. |

Preparation:

The active ingredient and excipients are dissolved in a sufficient quantity of distilled water and the solution is brought to the desired concentration by means of the necessary quantity of water. The solution is filtered and filled into 2 ml-ampules under aseptic conditions. Each ampule contains 50 mg of active ingredient.

EXAMPLE 15

Capsules

The capsule filler composition is compounded from the following ingredients:

| | |
|---|---|
| N—[N—(L-1-Methoxycarbonyl-3-phenyl-propyl)-alanyl]-L-2,3,4,9-tetrahydro-1H—pyrido[3,4-b]indole-3-carboxylic acid | 100.0 parts |
| Lactose | 250.0 parts |
| Corn starch | 40.0 parts |
| Talc | 10.0 parts |
| Total | 400.0 parts |

Preparation:

The active ingredient, lactose and corn starch are first mixed in a mixer and then in a comminuting machine. The mixture is introduced into the mixer again, mixed thoroughly with the talc, and 400 mg-portions are filled into hard gelatin capsules by machine. Each capsule contains 100 mg of active ingredient.

EXAMPLE 16

Suppositories

The suppository composition is compounded from the following ingredients:

| | |
|---|---|
| N—[N—(L-1-carboxy-3-phenylpropyl)-L-alanyl]-2,3,4,9-tetrahydro-1H—pyrido[3,4-b]indole-L-1-carboxylic acid | 100.0 parts |
| Cocoa butter (m.p. 36–37° C.) | 1600.0 parts |
| Carnabua wax | 100.0 parts |
| Total | 1800.0 parts |

Preparation:

The cocoa butter and carnabua wax are melted, mixed thoroughly and cooled to 45° C. The finely pulverized active ingredient is stirred into this mixture. Subsequently, 1.8 g-portions of the mixture are poured into slightly precooled suppository molds of suitable size and allowed to cool. Each suppository contains 100 mg of active ingredient.

Any one of the other compounds embraced by formula I or a non-toxic, pharmacologically acceptable salt thereof may be substituted for the particular active ingredient in Examples 12 through 16. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula $$R_1-CH-NH-CH-C-N \underset{COOR_2}{\overset{R_3\ O}{|\ \|}} \underset{}{\diagdown} \text{COOH, thieno-S ring}$$

wherein $R_1$ is hydrogen, alkyl of 1 to 6 carbon atoms or phenyl(alkyl of 1 to 6 carbon atoms);

$R_2$ is hydrogen, alkyl of 1 to 4 carbon atoms or phenyl(alkyl of 1 to 6 carbon atoms);

$R_3$ is hydrogen or alkyl of 1 to 6 carbon atoms; or a non-toxic, pharmaceologically acceptable salt thereof.

2. A compound of claim 1, where all of the centers of asymmetry are in the L-configuration.

3. A compound of claim 1, which is N-[N-(L-1-ethoxycarbonyl-3-phenylpropyl)-L-alanyl-]-4,5,6,7-tetrahydro-thieno[3,2-c]pyridine-L-4-carboxylic acid or a non-toxic, pharmacologically acceptable salt thereof.

4. A compound of claim 1, which is N-[N-(L-1-carboxy-3-phenylpropyl)-L-alanyl]-4,5,6,7-tetrahydro-thieno[3,2-c]pyridine-L-4-carboxylic acid or a non-toxic, pharmacologically acceptable salt thereof.

5. A compound of claim 1, which is N-[N-(L-1-ethoxycarbonyl-3-phenylpropyl)-L-alanyl]-4,5-dihydro-thieno[3,2-c]pyridine-6-carboxylic acid or a non-toxic, pharmacologically acceptable salt thereof.

6. An antihypertensive pharmaceutical composition consisting essentially of an inert pharmaceutical carrier and an effective antihypertensive amount of a compound of claim 1.

7. The method of lowering the blood pressure of a warm-blooded animal in need thereof, which comprises perorally, parenterally or rectally administering to said animal an effective antihypertensive amount of a compound of claim 1.

* * * * *